US00PP30590P2

(12) United States Plant Patent
Nair

(10) Patent No.: US PP30,590 P2
(45) Date of Patent: Jun. 25, 2019

(54) ***CITRUS* PLANT NAMED 'FIRST CANADIAN GOLDEN'**

(50) Latin Name: ***Citrus* hybrid**
Varietal Denomination: First Canadian Golden

(71) Applicant: Madhavan M. P. Nair, Grasswood (CA)

(72) Inventor: Madhavan M. P. Nair, Grasswood (CA)

( * ) Notice: Subject to any disclaimer, the term of this patent is extended or adjusted under 35 U.S.C. 154(b) by 0 days.

(21) Appl. No.: 15/932,591

(22) Filed: Mar. 19, 2018

(51) Int. Cl.
*A01H 5/08* (2018.01)

(52) U.S. Cl.
USPC ..... Plt./201

(58) Field of Classification Search
USPC ..... Plt./201
See application file for complete search history.

(56) References Cited

PUBLICATIONS

PLUTO Plant Variety Database Jan. 8, 2019.*

* cited by examiner

*Primary Examiner* — Annette H Para
(74) *Attorney, Agent, or Firm* — Penny J. Aguirre

(57) ABSTRACT

A new cultivar of *Citrus*, 'First Canadian Golden', that is characterized by its low light tolerance when grown in a home windowsill without supplemental lighting in small containers, its fruit that is similar in quality to high quality commercial limes and essentially seedless, its fruit with a skin thickness of 5 to 6 mm and an average Brix of 10°, its exhibits small leaves and a dwarf, bushy plant habit that is ideal for small container windowsill culture in homes and commercial buildings in cold climates and suitable to be grown as a bonsai tree, its ability to grow well and produce quality fruit in hydroculture, its mature fruit that typically has a conspicuous style and stigma, its dense flower clusters of 4 to 8 flowers and 12 fruit per year, and its multiple cycles of blooms and fruit set per year (3 to 4 cycles).

3 Drawing Sheets

Botanical classification: *Citrus* hybrid.
Varietal denomination: 'FIRST CANADIAN GOLDEN'.

CROSS REFERENCE TO A RELATED APPLICATION

This application is related to a Canadian plant breeders' rights application filed on Jun. 24, 2016, application No. 16-8946. There have been no offers for sale anywhere in the world prior to the effective filing date of this Application and no accessibility to one of ordinary skill in the art could have been derived from the printed plant breeder's rights documents.

BACKGROUND OF THE INVENTION

The present invention relates to a new and distinct cultivar of *Citrus* plant, botanically of hybrid origin and known as *Citrus* 'First Canadian Golden' and will be referred to hereafter by its cultivar name, First Canadian Golden'. The new cultivar represents a new dwarf lime plant that is grown for use in homes under low light conditions.

The new cultivar was derived from an ongoing controlled breeding program conducted by the Inventor in Saskatoon, Saskatchewan, that commenced in 1981. The overall purpose of the breeding program is the creation of a new type of dwarf lime trees and other hybrid *Citrus* trees that exhibit the fruit quality of commercial varieties that are also Low Light Tolerant [LLT] and can be grown in homes on indoor windowsills in small 6-inch containers with only natural available light.

The new cultivar arose from a cross made in April of 1991 between an unnamed and unpatented proprietary plant from the Inventor's breeding program designated as "CLX-1" (*Citrus medica* x *Citrus limonia*) as the female parent and *Citrus aurantifolia* 'Key Lime' (not patented) as the male parent. 'First Canadian Golden' was selected as a single unique plant amongst the seedlings from the above cross in October of 2010.

Asexual propagation of the new cultivar was first accomplished by stem cuttings in Saskatoon Canada, by the Inventor in October of 2010. Asexual propagation by stem cuttings has been determined that the characteristics of this cultivar are stable and are true to type in successive reproductions.

SUMMARY OF THE INVENTION

The following traits have been repeatedly observed and represent the unique characteristics of the new cultivar of *Citrus*. Trials were conducted over many years in Saskatoon, Saskatchewan, Canada.

1. 'First Canadian Golden' exhibits low light tolerance when grown in a home windowsill without supplemental lighting in small 6-inch containers.
2. 'First Canadian Golden' exhibits fruit that is similar in quality to high quality commercial limes and is essentially seedless (an occasionally seed may arise as the plant is apomictic).
3. 'First Canadian Golden' exhibits fruit with a skin (epicarp and mesocarp) thickness of 5 to 6 mm.

4. 'First Canadian Golden' exhibits fruit with an average Brix of 10°.
5. 'First Canadian Golden' exhibits small leaves and a dwarf, bushy plant habit that is ideal for small container windowsill culture in homes in cold climates, and suitable to be grown as a bonsai tree.
6. 'First Canadian Golden' exhibits good fruit production indoors in homes and commercial buildings where the atmospheric temperature is within 55 to 75° F. and the available light level is of typical of indoor spaces (75-200 μmol/m2/s).
7. 'First Canadian Golden' exhibits the ability to grow well and produce quality fruit in hydroculture.
8. 'First Canadian Golden' exhibits mature fruit that typically has a conspicuous style and stigma.
9. 'First Canadian Golden' exhibits dense corymbs of up to 8 flowers.
10. 'First Canadian Golden' produces up to 12 fruits per year in a 6-inch container.
11. 'First Canadian Golden' exhibits multiple cycles of blooms and fruit set per year (3 to 4 cycles).

The female parent of 'First Canadian Golden', "CLX-1", differs from 'First Canadian Golden' in having fruit that is larger in size, has a conspicuous extended style and stigma, has skin that is thicker and rougher, and juicier. The male parent of 'First Canadian Golden', *Citrus aurantifolia* 'Key Lime', differs from 'First Canadian Golden' in lacking multiple blooms and fruit cycles per year and in failure to to thrive when grown under low light conditions and in containers indoors as it requires the outdoor growing conditions in *Citrus* growing areas.

'First Canadian Golden' is unique in its ability to grow and set fruit under low light conditions and the Inventor has not had success in growing any other lime cultivars known in the trade to him under the same conditions. 'First Canadian Golden' can be compared to an unnamed and unpatented sister seedling of 'First Canadian Golden', designated "KLX-4". "KLX-4" differs from 'First Canadian Golden' in having a larger plant size and low fruit productivity and fruit that are larger, produce many seeds, have a thicker rind, and are of poor quality.

BRIEF DESCRIPTION OF DRAWINGS

The accompanying color photographs illustrate the distinguishing characteristics of the new cultivar 'First Canadian Golden'.

The photographs in FIG. 1, FIG. 4 and FIG. 5 were taken of plants (and plant parts) 27 years in age as grown in a container (12" in length, 12" in width, 20" in height) in a greenhouse in Saskatoon, Saskatchewan, Canada.

Figure 2:
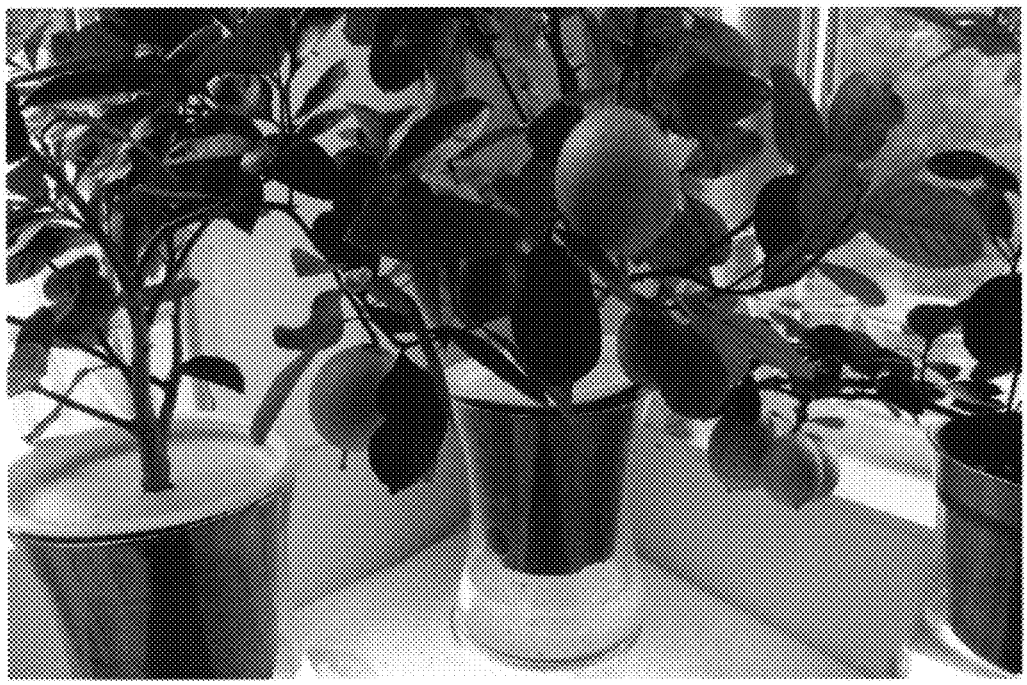
Figure 3:
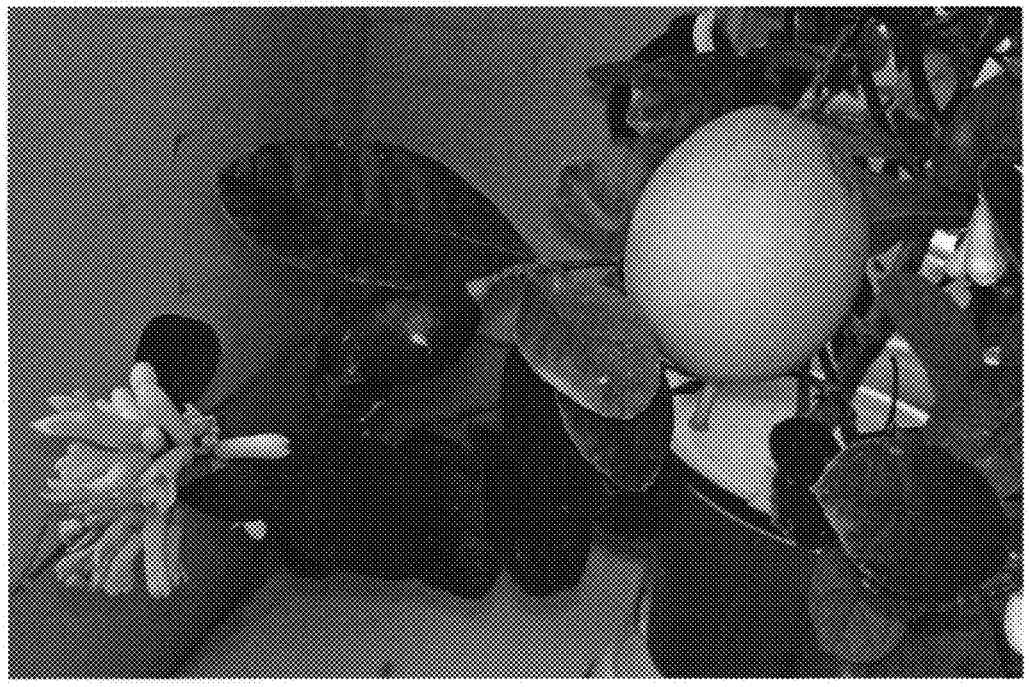

The photographs in FIG. 2 and FIG. 3 were taken of plants (and plant parts) about 2 years in age as grown indoors on a home windowsill in 6-inch containers in Grasswood, Saskatchewan, Canada.

Figure 1:
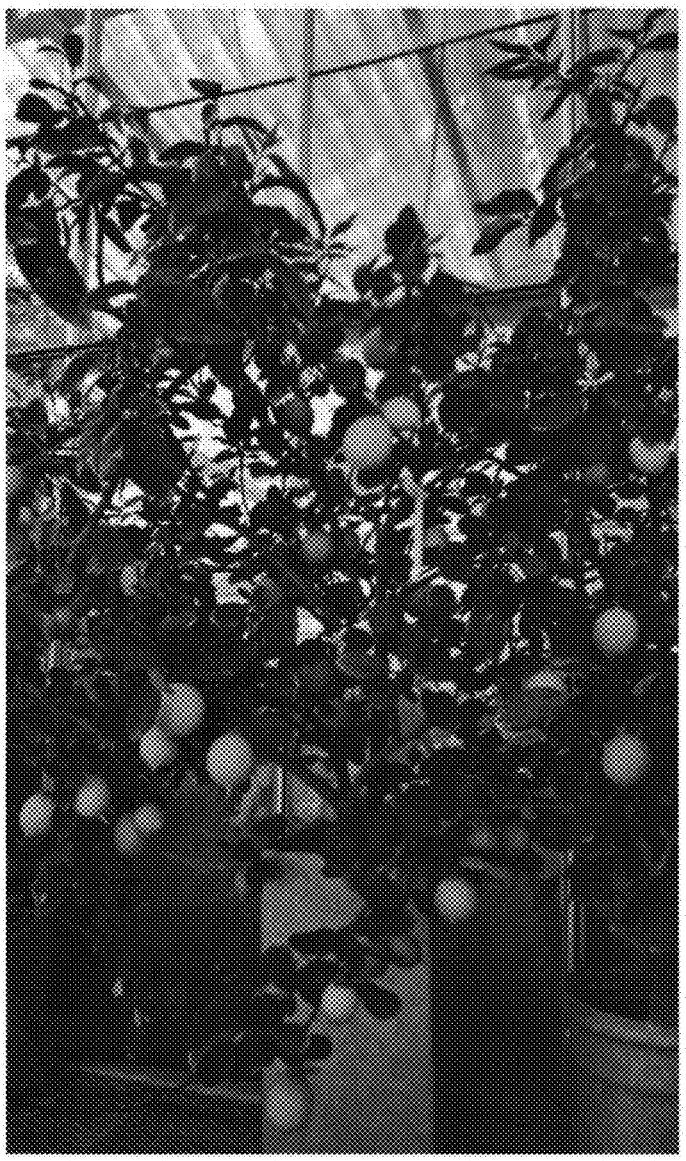

The photograph in FIG. 1 provides a view of the dwarf habit of a 27 year-old plant of 'First Canadian Golden'.

The photograph in FIG. 2 provides a view of 'First Canadian Golden' growing in a windowsill.

The photograph in FIG. 3 provides a view of the multiflowering and fruiting of 'First Canadian Golden'.

Figure 4:
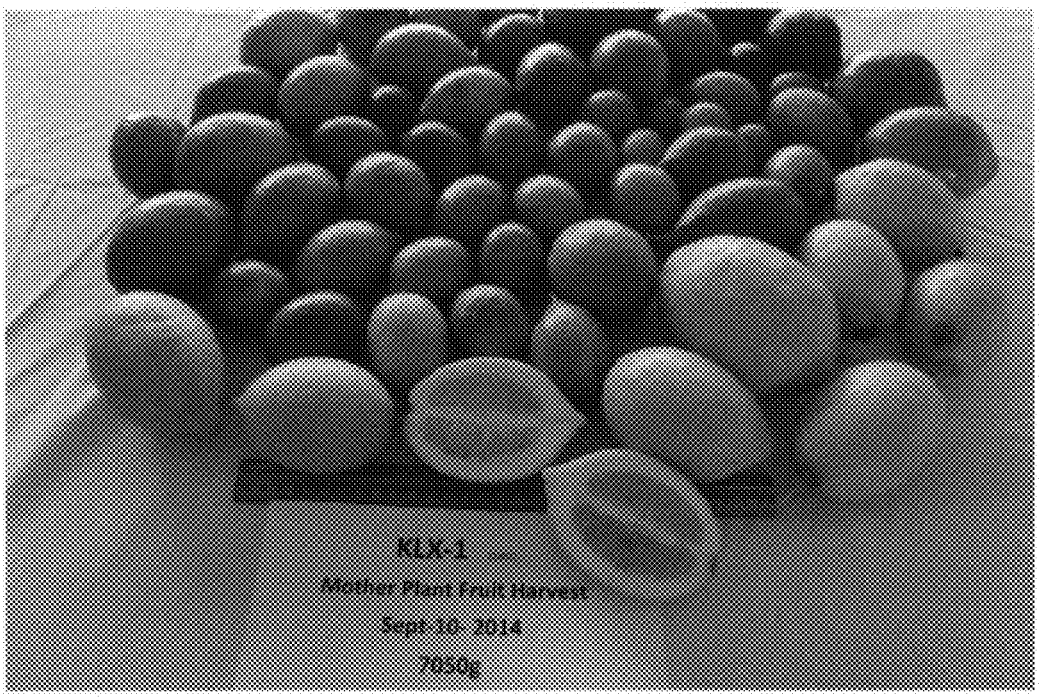

The photograph in FIG. 4 provides a view of fruit harvested in different stages of maturity of 'First Canadian Golden'.

Figure 5:
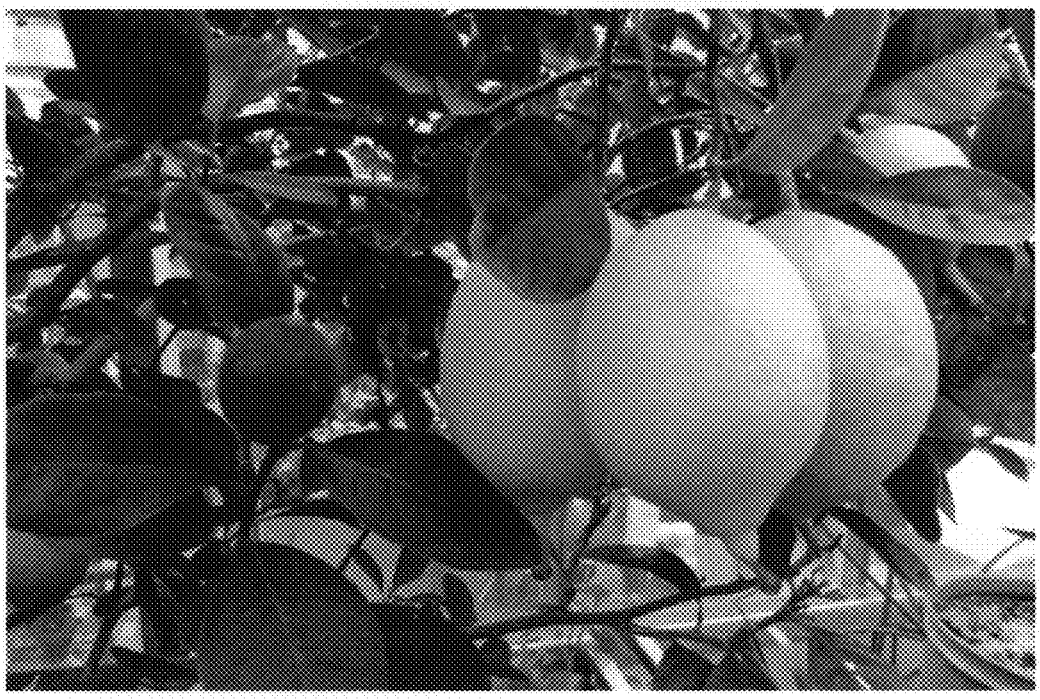

The photograph in FIG. 5 a view of the fruit on a mature plant of 'First Canadian Golden'.

The colors in the photographs may differ slightly from the color values cited in the detailed botanical description, which accurately describe the colors of the new *Citrus*.

DETAILED BOTANICAL DESCRIPTION OF THE PLANT

The following is a detailed description of 1 to 2-year-old plants of the new cultivar as grown indoors under low light in containers in a greenhouse in Saskatoon, Saskatchewan, Canada. The phenotype has been observed to be consistent when grown under constant indoor temperature, variable day length, natural reflected light intensity, and proper water and fertility levels. However, the phenotype of the new cultivar may vary with variations in environmental and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Tree type.*—Sub-tropical bush, evergreen, lime.

*Tree habit.*—Dwarf, upright, rounded, bushy plant habit, can be controlled by pruning for suitable indoor growing area and shape.

*Tree size.*—Average of 1.2 m in height and 0.9 m in width after 27 years of growth in a 3 cubic foot container, outdoor trials in subtropical or tropical environments has not been conducted.

*Growth rate.*—Slow to moderate in a 6-inch container.

*Diseases.*—Although the new cultivar has been observed to be disease free, no susceptibility or resistance to diseases can be claimed as there is no *Citrus* diseases pressure in Canada as they are not naturally grown there.

*Pests.*—No resistance to pests has been observed, control measures may be necessary to treat or avoid insect problems that commonly effect houseplants and greenhouse grown plants.

*Hardiness.*—Grown as an indoor plant only, outdoor trials have not been conducted to date.

*Environmental conditions.*—Performs extremely well in constant temperatures in indoor windows of homes without the addition of any artificial light.

*Propagation.*—Stem cuttings, budding onto rootstock has not been tested.

*Root development.*—Roots initiate in an average of 21 days under mist and bottom heat and becomes fully rooted in 4 to 6 weeks as a young plant, plants will bloom and set fruit in 4 months to one year depending on the stem location of the stem cuttings (tip or tender shoot cuttings require about one year).

*Growth rate.*—Slow to moderate in a 6-inch container.

Branch description:

*Trunk description.*—Two main trunks, up to 5 cm in diameter as observed 5 cm above soil level on a 27 year-old plant.

*Branching habit.*—Pruning the plant can produce any desirable shape from the main stem.

*Branch strength.*—Adequate to support the heavy load of the fruits, even on a small plant.

*Branch surface.*—Smooth and shiny on new growth, becomes slightly rough and finely ridged as it matures.

*Internode length.*—An average of 2 cm.

Description of dormant shoots:

*Branch appearance.*—Flattened to slightly oval on new growth.

*Branch strength.*—Strong and flexible, not brittle does not break easily.

*Branch size.*—Highly variable in length and 1 to 3 mm in width.

*Branch surface.*—Smooth bark for the first year, then becoming finely ridged.

*Branch internode length.*—Average of 2 to 4 cm.

*Branch color.*—138A.

*Shoot angle.*—Approximately 45°.

Description of growing shoots:

*Color of shoot.*—Emerging; 140A, mature; color between 138A and 137B.

*Shoot size.*—Highly variable in length and an average of 3 cm in width.

*Shoot surface.*—Glabrous.

Foliage description:

*Leaf orientation.*—Upward to outward with aspect slightly cupped inward (also influenced by light source).

*Leaf division.*—Simple.

*Leaf shape.*—Elliptic.

*Leaf arrangement.*—Irregular.

*Leaf size.*—Average of 10 cm in length and 4 to 4.5 cm in width (leaves are smaller towards the tip and under higher light).

*Leaf apex.*—Acuminate.

*Leaf base.*—Cuneate.

*Leaf surface.*—Glabrous and satiny on both surfaces, speckled with minutely translucent oil glands.

*Leaf texture.*—Thick and leathery.

*Leaf margin.*—Crenulate at 3 to 5 mm intervals.

*Leaf color.*—Upper surface emerging leaves; 138C, upper surface mature leaves; 138A, lower surface emerging leaves; 138D, lower surface mature leaves; 139B.

*Leaf venation.*—Pinnate, upper surface 138A in color, lower surface prominently raised main vein and slightly raised lateral veins, 138A.

*Petiole.*—Slightly winged near leaf base, average of 2 to 4 mm in length, wings 1 mm in width, both surfaces 138A in color, both surfaces glabrous.

*Durability of foliage to stress.*—Returns from minor wilt with no damage.

*Thorns.*—Minimal, attachment is superior to leaf petiole and lateral to bud, average of 1 to 1.5 cm in length, 0.5 to 1 mm in diameter, color; 138A at base, 170B towards apex.

Flower description:

*Flowering period.*—Average of every 90 to 120 days, will bloom indoors up to 3 to 4 times per year, cuttings will bloom immediately or 3 to 4 months and later depending on the location of the cuttings on the stem.

*Number of flowers.*—Ranges from 1 to 8 per inflorescence depending on flowering cycle.

*Inflorescence type.*—Corymb borne on axillary nodes.

*Inflorescence size.*—Following a new flush of growth with 2 to 4 small leaves, the total length of growth is about 2 to 3 inches long with 6 to 8 flower buds (corymb). It is noted on other flowering cycles; the inflorescence is as short as 1 inch without leaves and may only have 1 to 3 flower buds.

*Flower buds.*—Oblong in shape, NN155B in color, average of 2 cm in length and 5 to 6 mm in diameter, glabrous surface.

*Flower size.*—An average of 2 to 2.5 cm in length and 7 mm in width.

*Flower fragrance.*—Mildly sweet, lemon-like, flower buds and flowers can be used to make tea).

*Flower aspect.*—Upright and outward.

*Petals.*—5 per flower, un-fused but do not fully open, surround the pistil, elliptic in shape and recurved, acute apex, truncate base, entire margin, average of 1.8 cm in length and 5 mm in width, color of upper and lower surface NN155B, both surfaces are satiny, waxy, glabrous, and thick substance.

*Calyx.*—Fused sepals, circular, cupped around ovary, 5 to 7 mm in diameter, an average of 2 mm in depth, waxy surface.

*Peduncle.*—138A in color, average of 2 to 4 cm in length and 1.5 mm in width, waxy surface.

*Pedicel.*—An average of 2 mm in width and length, 138A in color, waxy surface.

Reproductive organs:

*Hypogynium.*—Small barely visible to the naked eye.

*Gynoecium.*—Pistil; 1, 1.8 to 2 cm in length (including ovary), stigma; 5 mm in diameter, 151D in color, style; 8 to 11 mm in length, 145C in color, ovary; 7 mm in width, 150D in color.

*Androecium.*—Stamens; 24, filaments; 8 mm in length, fused into upright ring, 155C in color, anther; spear shaped, 1.5 to 2 mm in length, 7A in color, pollen; moderate in quantity, dry and powdery, 20B in color.

Fruit description:

*Fruit harvest.*—Grown indoors, the plant blooms year-round and fruits in various stages of development are present, on average it flowers every 3 months with 3 to 4 crops per year.

*Skin (rind).*—5 to 6 mm in thickness, 4B in color, outer layer (exocarp); pitted, glossy, epicarp with oil glands (medium pits), average of 2 to 3 mm in thickness, inner surface (mesocarp or albedo); fibrous, 155B in color, average of 3 mm in thickness.

*Fruit segments.*—9 to 10, an average of 4 to 5 cm in length and 1.5 to 2.25 cm in width.

*Fruit brix.*—Average of 10°.

*Fruit set.*—Heavy, best to thin out the flowers when blooming.

*Seed.*—0 seeds per section and 0 seeds per fruit (seedless).

*Fruit type.*—Hesperidium.

*Fruit size.*—Average of 5 to 6 cm in diameter, 6 to 6.5 cm in length.

*Fruit shape.*—Spheroid with an extended style and pistil 5 to 7 mm long.

*Fruit symmetry.*—Roughly symmetrical from left to right hemisphere, and top to bottom hemisphere with extended style with stigma at the distal end of the fruit, truncated at the proximal end (the base of the fruit).

*Fruit flavor.*—Tart, as a lime and lemon hybrid plant it produces the aroma, taste and juice quality of a lime.

*Fruit weight.*—Average of 90 to 110 grams.

*Fruit aroma.*—Strong lime scented.
*Fruit flesh color.*—4B with endocarp partitions 155B.
*Color of axis.*—155B.
*Flesh texture.*—Glossy, juicy.
*Naval presence.*—None, instead of a navel, a style and stigma is present on the majority of fruit.
*Juice production.*—Average of 20 to 30 ml per fruit.
*Fruit keeping quality.*—Average of 2 to 3 weeks at room temperature before rind begins to mummify and fruit volume begins to shrink from dehydration, 6 to 8 weeks if refrigerated with humidity control, on the plant the fruit will stay for many months with good amount of juice till harvested, eventually it dehydrates and will shrivel.
*Fruit shipping quality.*—Reasonably thick skinned and suitable packing materials may be used to transport.
*Fruit use.*—Primarily for fresh consumption at home and processing to pickles rind for candy making, not intended for commercial juicing.

It is claimed:

1. A new and distinct variety of *Citrus* tree named 'First Canadian Golden' as described and illustrated herein.

* * * * *